US011534107B2

(12) United States Patent
Thakur et al.

(10) Patent No.: US 11,534,107 B2
(45) Date of Patent: Dec. 27, 2022

(54) SYSTEMS AND METHODS FOR THERAPY TITRATION IN HEART FAILURE

(71) Applicant: Cardiac Pacemakers, Inc., St. Paul, MN (US)

(72) Inventors: Pramodsingh Hirasingh Thakur, Woodbury, MN (US); Viktoria A. Averina, Shoreview, MN (US); Yi Zhang, Plymouth, MN (US); Qi An, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 748 days.

(21) Appl. No.: 16/111,019

(22) Filed: Aug. 23, 2018

(65) Prior Publication Data

US 2019/0083030 A1 Mar. 21, 2019

Related U.S. Application Data

(60) Provisional application No. 62/561,004, filed on Sep. 20, 2017.

(51) Int. Cl.
*A61B 5/00* (2006.01)
*A61N 1/362* (2006.01)
(Continued)

(52) U.S. Cl.
CPC ........ *A61B 5/4839* (2013.01); *A61B 5/02055* (2013.01); *A61B 5/7275* (2013.01);
(Continued)

(58) Field of Classification Search
CPC ............... A61B 5/4839; A61B 5/7275; A61M 5/14276; A61M 5/1723;
(Continued)

(56) References Cited

U.S. PATENT DOCUMENTS

| 2007/0129643 | A1* | 6/2007 | Kwok | ................. | A61B 5/0816 600/529 |
| 2009/0299156 | A1* | 12/2009 | Simpson | ............. | A61M 5/1723 600/301 |

(Continued)

FOREIGN PATENT DOCUMENTS

WO   WO-2017125682 A1 *  7/2017  ........... A61B 5/4839

*Primary Examiner* — Kami A Bosworth
*Assistant Examiner* — Leah J Swanson
(74) *Attorney, Agent, or Firm* — Schwegman Lundberg & Woessner, P.A.

(57) ABSTRACT

Systems and methods for treating a medical condition such as worsening heart failure (WHF) are described. A medical system may sense one or more physiological signals, and generate from the sensed physiological signals a signal metric trend indicating a progression of heart failure. A detector may detect a physiological event leading to WHF. A therapy control circuit may generate a therapy titration protocol using the generated signal metric trend. The therapy titration protocol includes a temporal profile of therapy dosage relative to a target dosage. The therapy control circuit may adjust the target dosage based on patient response. Therapies may be administered by a clinician or automatically delivered to the patient according to the therapy titration protocol.

12 Claims, 8 Drawing Sheets

(51) Int. Cl.
*A61N 1/365* (2006.01)
*A61M 5/172* (2006.01)
*A61M 5/142* (2006.01)
*A61B 5/0205* (2006.01)

(52) U.S. Cl.
CPC ...... *A61M 5/14276* (2013.01); *A61M 5/1723* (2013.01); *A61N 1/365* (2013.01); *A61N 1/3627* (2013.01); *A61M 2205/3576* (2013.01); *A61M 2205/505* (2013.01); *A61M 2230/04* (2013.01); *A61M 2230/20* (2013.01); *A61M 2230/201* (2013.01); *A61M 2230/42* (2013.01); *A61M 2230/50* (2013.01)

(58) Field of Classification Search
CPC .... A61M 2205/3576; A61M 2205/505; A61M 2230/04; A61M 2230/20; A61M 2230/201; A61M 2230/42; A61M 2230/50; A61N 1/3627; A61N 1/365
See application file for complete search history.

(56) References Cited

U.S. PATENT DOCUMENTS

| | | | |
|---|---|---|---|
| 2013/0178786 A1* | 7/2013 | Wariar | A61N 1/36578 604/20 |
| 2015/0032053 A1* | 1/2015 | Schmitz | G06F 19/3468 604/151 |
| 2015/0351660 A1* | 12/2015 | An | G16H 40/67 600/484 |
| 2017/0095160 A1 | 4/2017 | Thakur et al. | |
| 2019/0030245 A1* | 1/2019 | Baviere | G16H 20/10 |

\* cited by examiner

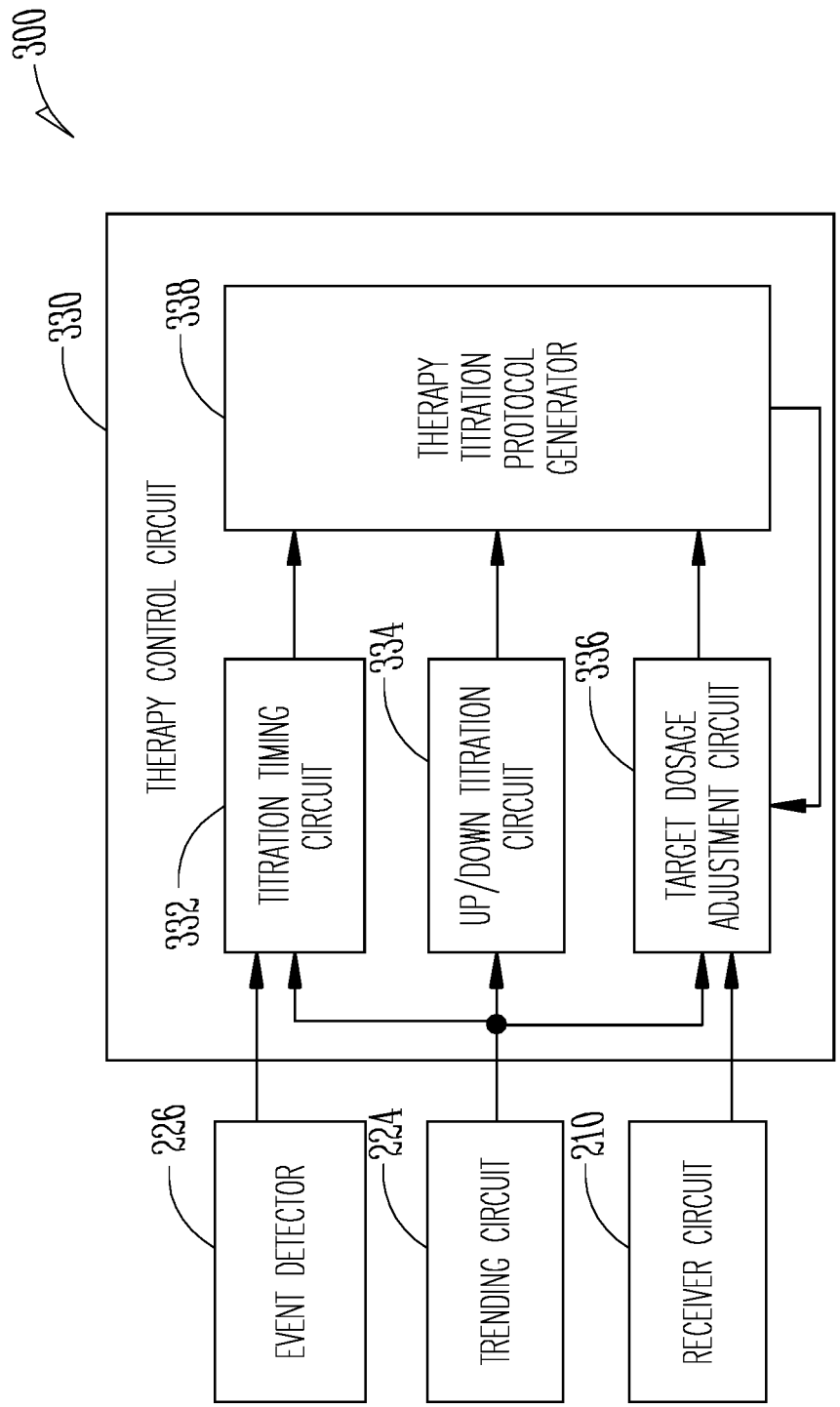

SYSTEMS AND METHODS FOR THERAPY TITRATION IN HEART FAILURE

CLAM OF PRIORITY

This application claims the benefit of priority under 35 U.S.C. § 119(e) of U.S. Provisional Patent Application Ser. No. 62/561,004, filed on Sep. 20, 2017, which is herein incorporated by reference in its entirety.

TECHNICAL FIELD

This document relates generally to medical systems, and more particularly, to systems, devices and methods for titrating therapy dosage in heart failure.

BACKGROUND

Congestive heart failure (CHF or HF) is a major health problem and affects many people in the United States alone. CHF patients may have enlarged heart with weakened cardiac muscles, resulting in poor cardiac output of blood. Although CHF is usually a chronic condition, it may occur suddenly. It may affect the left heart, right heart or both sides of the heart. If CHF affects the left ventricle, signals that control the left ventricular contraction are delayed, and the left and right ventricles do not contract simultaneously. Non-simultaneous contractions of the left and right ventricles may decrease the pumping efficiency of the heart.

In many CHF patients, elevated pulmonary vascular pressures may cause fluid accumulation in the lungs over time. The fluid accumulation may precede or coincide with worsening heart failure (WHF), such as a HF decompensation event. WHF may be characterized by pulmonary or peripheral edema, reduced cardiac output, and symptoms such as fatigue, shortness of breath, and the like.

CHF may be treated by medical therapy, or by an implantable medical device (IMD) that may provide electrostimulation therapy. An IMD can monitor patient health condition such as progression of CHF, and deliver electrostimulation to restore or improve cardiac performance, or to rectify cardiac arrhythmias. One example of electrostimulation therapy is resynchronization therapy (CRT), which involves electrostimulation of both left and right ventricles to promote synchronous pumping between both ventricles. Medical therapy for treating CHF may involve one or more medications, such as diuretics to reduce edema, Angiotensin-converting enzyme (ACE) inhibitors or Angiotensin II receptor blockers to promote vasodilation and therefore improve blood flow and decrease heart workload, inotropes to improve heart pumping function and maintain blood pressure, or digoxin to increase the strength of myocardial contraction and to slow the heartbeat, among other medications. Device therapy and medical therapy may be titrated to reduce morbidity and mortality in CHF.

Overview

Frequent monitoring of CHF patients and timely detection of events indicative of WHF may help reduce healthcare cost associated with HF hospitalization. Identification of patient at an elevated risk of developing WHF may help ensure timely treatment, improve the prognosis and patient outcome, and avoid unnecessary medical interventions and save the overall cost.

Ambulatory medical devices (AMDs) may be used for monitoring HF patient and detecting WHF events. Examples of such ambulatory medical devices may include implantable medical devices (IMD), subcutaneous medical devices, wearable medical devices or other external medical devices. An AMD may include sensors to sense physiological signals. An AMD may detect a WHF event based on a temporal change in a physiological signal, or a temporal change in measurements of composite metric derived from a number of physiological signals. When the physiological signal or the composite metric crosses respective detection thresholds, an alert may be generated to warn a clinician of an on-going or future WHF event. The AMD can deliver therapy such as electrostimulation or administer medications to target tissues or organs, automatically or with a clinician intervention, to restore or improve patient cardiac function.

Timely titration of HF therapies, including electrostimulation therapy or medications, to accommodate changes in patient HF status and comorbidities is important in HF patient management. However, therapy titration can be challenging, partly because HF patients frequently have multiple co-morbidities, need to take numerous medications, and often move between acute and primary health-care sectors. Lack of a clear, patient-specific titration plan, along with patient adherence issues due to the changing medication regimen, and inefficient communication of medication plans between acute and primary care, many affect therapy titration. Additionally, organizing frequent clinic visits to evaluate patient therapy responses can be practically difficult for some patients. As a result, dosages are often not optimized in clinical practice. The present inventors have recognized there remains a need for technological solutions that may improve HF therapy titration for better patient outcome. In particular, the present inventors have recognized that the physiological signals or composite metric measurements, which are used for detecting events leading to WHF, may be used for titrating HF therapy. The individualized therapies or interventions tailored to specific patient conditions based on the physiological signals or composite metric requires little to no additional cost or system complexity.

Embodiments of the present subject matter provide systems, devices, and methods for adjusting therapy dosage for treating a medical condition such as WHF. A medical system may sense one or more physiological signals, and generate from the sensed physiological signals a signal metric trend indicating a progression of a physiological condition such as WHF. An event detector may detect a physiological event leading to WHF. A therapy control circuit may generate a therapy titration protocol using the signal metric trend. The therapy titration protocol includes a temporal profile of therapy dosage relative to a target dosage. Therapies may be administered by a clinician or automatically delivered to the patient according to the therapy titration protocol.

Example 1 is a system for adjusting a therapy dosage in a patient. The system comprises a receiver circuit configured to receive one or more physiological signals, a physiological event detector circuit configured to generate, from the sensed one or more physiological signals, a signal metric trend indicating a progression of a physiological condition, and to detect a physiological event using the generated signal metric trend, and a therapy control circuit that is coupled to the physiological event detector circuit and configured to generate a therapy titration protocol using the generated signal metric trend. The therapy titration protocol may include a temporal profile of therapy dosage relative to a target dosage.

In Example 2, the subject matter of Example 1 optionally includes a therapy delivery unit that may initiate or adjust a therapy according to the therapy titration protocol in response to the detection of the physiological event.

In Example 3, the subject matter of any one or more of Examples 1-2 optionally includes the physiological event detector circuit that may detect a worsening heart failure (WHF) event. The therapy control circuit may generate a heart failure therapy titration protocol using the generated signal metric trend.

In Example 4, the subject matter of Example 3 optionally includes the heart failure therapy titration protocol that may include a temporal profile of drug dosage relative to a target drug dosage for treating the detected WHF.

In Example 5, the subject matter of any one or more of Examples 1-4 optionally includes the therapy control circuit that may up-titrate the therapy dosage when the generated signal metric trend indicates a sustained worsening of the physiological condition.

In Example 6, the subject matter of Example 5 optionally includes the therapy control circuit that may up-titrate the therapy dosage in response to the generated signal metric trend exceeding a physiological event onset threshold and indicating an increase trend.

In Example 7, the subject matter of any one or more of Examples 1-6 optionally includes the therapy control circuit that may down-titrate the therapy dosage when the generated signal metric trend indicates lack of a sustained worsening of the physiological condition.

In Example 8, the subject matter of Example 7 optionally includes the therapy control circuit that may down-titrate the therapy dosage in response to the generated signal metric trend falling below a specific threshold and indicating a decrease trend.

In Example 9, the subject matter of any one or more of Examples 1-8 optionally includes the temporal profile of therapy dosage that may include a stepwise up-titration or a stepwise down-titration of the therapy dosage.

In Example 10, the subject matter of any one or more of Examples 1-9 optionally includes the therapy control circuit that may adjust the target dosage using a comparison of the temporal profile of therapy dosage and the target dosage.

In Example 11, the subject matter of Example 10 optionally includes the therapy control circuit that may increase the target dosage when the temporal profile of therapy dosage is above the target dosage for a first time period.

In Example 12, the subject matter of Example 11 optionally includes the therapy control circuit that may increase the target dosage to a level corresponding to a lowest therapy dosage achieved during the first time period.

In Example 13, the subject matter of Example 10 optionally includes the therapy control circuit that may down-titrate the therapy dosage to a level lower than the target dosage, evaluate patient response to the down-titrated therapy dosage over a second time period, and decrease the target dosage to a level corresponding to the down-titrated therapy dosage if the evaluated patient response indicates no worsening of the physiological condition during the second time period.

In Example 14, the subject matter of Example 13 optionally includes the patient response that may include a signal metric trend corresponding to the down-titrated therapy dosage. The therapy control circuit may decrease the target dosage if the signal metric trend is within a specific range indicating no worsening of the physiological condition during the second time period.

In Example 15, the subject matter of any one or more of Examples 1-14 optionally includes the therapy titration protocol that may include a set of instructions for adjusting patient therapy under specific conditions.

Example 16 is a method for adjusting a therapy dosage in a patient using a medical system. The method comprises steps of: receiving one or more physiological signals via a receiver circuit; generating, via a physiological event detector circuit, from the sensed one or more physiological signals a signal metric trend indicating a progression of a physiological condition; detecting a physiological event using the generated signal metric trend via the physiological event detector circuit; and generating a therapy titration protocol using the generated signal metric trend via the therapy control circuit, the therapy titration protocol that may include a temporal profile of therapy dosage relative to a target dosage.

In Example 17, the subject matter of Example 16 optionally includes initiating or adjusting a therapy according to the therapy titration protocol in response to the detection of the physiological event.

In Example 18, the subject matter of Example 16 optionally includes detecting the physiological event that may include detecting a worsening heart failure (WHF) event, and generating the therapy titration protocol that may include generating a heart failure therapy titration protocol using the generated signal metric trend.

In Example 19, the subject matter of Example 16 optionally includes generating a therapy titration protocol that may include one or more of: up-titrating the therapy dosage in response to the generated signal metric trend exceeding a physiological event onset threshold and indicating an increase trend; or down-titrating the therapy dosage in response to the generated signal metric trend falling below a specific threshold and indicating a decrease trend.

In Example 20, the subject matter of Example 16 optionally includes the temporal profile of therapy dosage that may include a stepwise up-titration or a stepwise down-titration of the therapy dosage.

In Example 21, the subject matter of Example 16 optionally includes adjusting the target dosage using a comparison of the temporal profile of therapy dosage and the target dosage.

In Example 22, the subject matter of Example 21 optionally includes adjusting the target dosage that may include, when the temporal profile of therapy dosage is above the target dosage for a first time period, increasing the target dosage to a level corresponding to a 1 dosage achieved during the first time period.

In Example 23, the subject matter of Example 21 optionally includes adjusting the target dosage that may include: down-titrating the therapy dosage to a level lower than the target dosage; evaluating patient response to the down-titrated therapy dosage over a second time period; and when the evaluated patient response indicates no worsening of the physiological condition during the second time period, decreasing the target dosage to a level corresponding to the down-titrated therapy dosage.

The systems, devices, and methods discussed in this document may improve the technology of therapy titration in patients with an AMD. A technological challenge in HF patient management is timely and individualized therapy titration based on frequent and effective patient monitoring. Continuous patient monitoring via the AMD allows for timely detection of changes in HF status and development of comorbidities. In addition to conventional ambulatory patient monitoring and medical diagnostic functionality (e.g., detecting a target physiological event such as WHF), the embodiments discussed herein further uses the physiological signals or composite metric measurements to tailor therapy according to an individualized therapy titration protocol. The therapy titration protocol determined based on the changes in physiological signals or composite metric measurements offers the advantage of individualized therapy tailored to specific patient conditions, which may lead to better treatment and patient management. For example, fewer unnecessary medical interventions, such as drugs, procedures, or device therapies, may be scheduled, prescribed, or provided to such patients. As a result, overall system cost savings may be realized. Additionally, the advantages of individualized dosage titration may come with little to no additional cost or system complexity, at least because the physiological signals or composite metric measurements are also used also for producing HF diagnostics.

The device-based therapy titration as discussed in this document may also improve the functionality of a patient management system or device. In some cases, improved therapy titration may be achieved without a modification of the hardware of an existing patient management system or an AMD. Memory usage may be more efficient by storing the therapy titration protocol that is clinically more relevant to patient management strategies. Storage of the therapy titration protocol requires limited memory storage and transmission bandwidth. A system or a device that generates and stores the therapy titration protocol may not only improve therapy efficacy and patient outcome, but may also reduce unnecessary device therapies, and extend battery life and AMD longevity.

Although the discussion in this document focuses therapy titration for WHF detected by AMDs, this is meant only by way of example and not limitation. It is within the contemplation of the inventors, and within the scope of this document, that the systems, devices, and methods discussed herein may also be used to detect, and alert occurrence of, cardiac arrhythmias, syncope, pulmonary congestion, respiratory disease, or renal dysfunctions, among other medical conditions. Additionally, although systems and methods are described as being operated or exercised by clinicians, the entire discussion herein applies equally to organizations, including hospitals, clinics, and laboratories, and other individuals or interests, such as researchers, scientists, universities, and governmental agencies, seeking access to the patient data.

This Overview is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIG. 3 illustrates generally an example of a therapy titration system generate a therapy titration protocol for treating a medical condition.

DETAILED DESCRIPTION

Disclosed herein are systems, devices, and methods for adjusting therapy dosage for treating a medical condition, such as worsening heart failure (WHF). A medical system may receive one or more physiological signals, and generate from the received physiological signals a signal metric trend indicating a progression of a physiological condition. A detector may detect a physiological event such as a WHF event. A therapy control circuit may use the generated signal metric trend to generate a therapy titration protocol that includes a temporal profile of therapy dosage relative to a target dosage. Therapies may be administered by a clinician or automatically delivered to the patient according to the therapy titration protocol.

Figure 1:
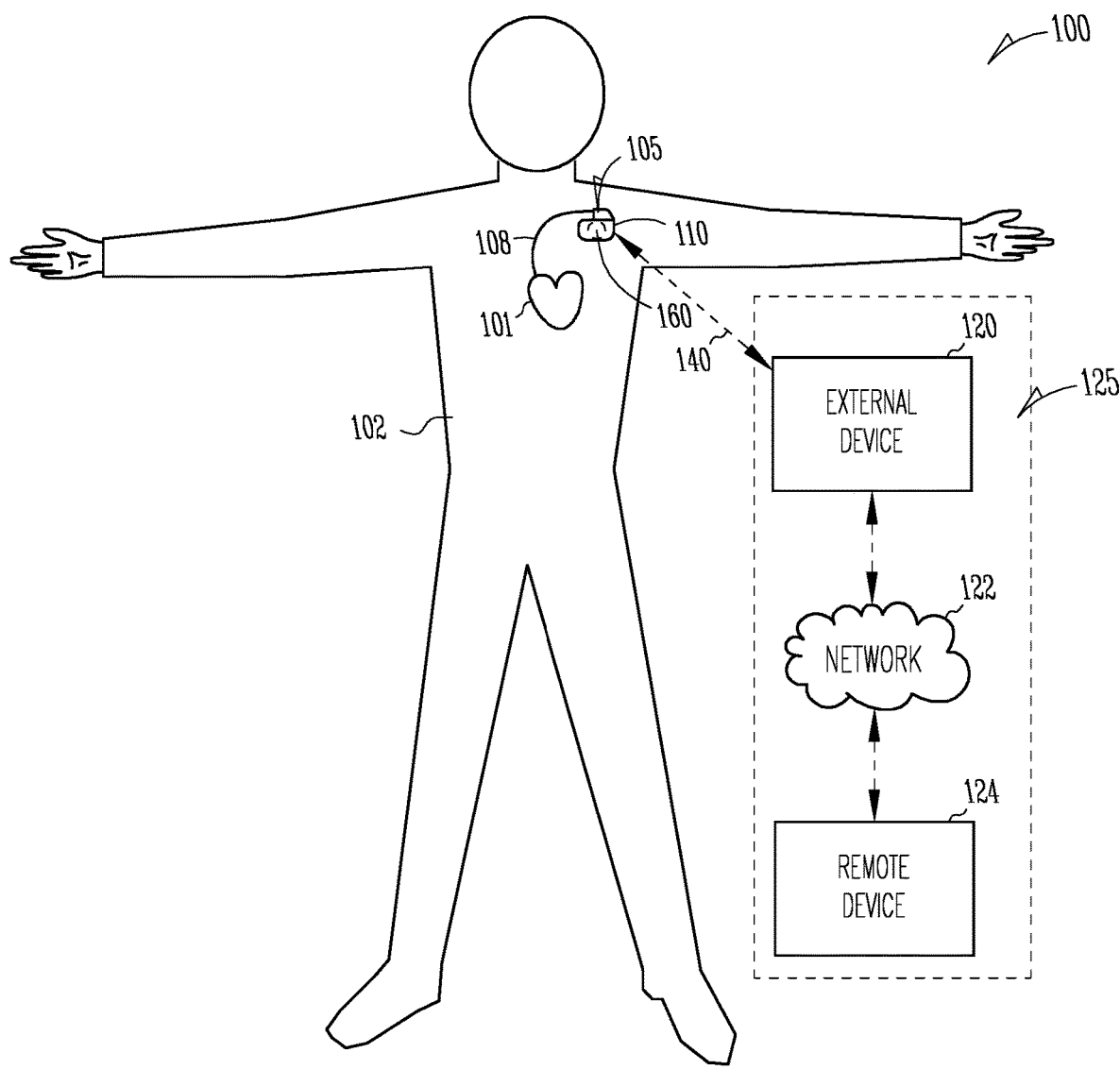
FIG. 1 illustrates generally an example of a patient management system and portions of an environment in which the system may operate.

FIG. 1 illustrates generally an example of a patient management system 100 and portions of an environment in which the system 100 may operate. The patient management system 100 may perform a range of activities, including remote patient monitoring, diagnosis of a disease condition, and providing information about therapy titration to rectify the disease condition and improve patient outcome. Such activities can be performed proximal to a patient, such as in the patient's home or office, through a centralized server, such as in a hospital, clinic or physician's office, or through a remote workstation, such as a secure wireless mobile computing device.

The patient management system 100 may include an ambulatory system 105 associated with a patient 102, an external system 125, and a telemetry link 115 providing for communication between the ambulatory system 105 and the external system 125.

The ambulatory system 105 may include an ambulatory medical device (AMD) 110. In an example, the AMD 110 may be an implantable device subcutaneously implanted in a chest, abdomen, or other parts of the patient 102. Examples of the implantable device may include, but are not limited to, pacemakers, pacemaker/defibrillators, cardiac resynchronization therapy (CRT) devices, cardiac remodeling control therapy (RCT) devices, neuromodulators, drug delivery devices, biological therapy devices, diagnostic devices such as cardiac monitors or loop recorders, or patient monitors, among others. The AMD 110 alternatively or additionally may include a subcutaneous medical device such as a subcutaneous monitor or diagnostic device, external monitoring or therapeutic medical devices such as automatic external defibrillators (AEDs) or Holter monitors, or wearable medical devices such as patch-based devices, smart watches, or smart accessories.

By way of example, the AMD 110 may be coupled to a lead system 108. The lead system 108 may include one or more transvenously, subcutaneously, or non-invasively placed leads or catheters. Each lead or catheter may include one or more electrodes. The arrangements and uses of the lead system 108 and the associated electrodes may be determined using the patient need and the capability of the AMD 110. The associated electrodes on the lead system 108 may be positioned at the patient's thorax or abdomen to sense a physiological signal indicative of cardiac activity, or physiological responses to diagnostic or therapeutic stimulations to a target tissue. By way of example and not limitation, and as illustrated in FIG. 1, the lead system 108 may be surgically inserted into, or positioned on the surface of, a heart 101. The electrodes on the lead system 108 may be positioned on a portion of a heart 101, such as a right atrium (RA), a right ventricle (RV), a left atrium (LA), or a left ventricle (LV), or any tissue between or near the heart portions. In some examples, the lead system 108 and the associated electrodes may alternatively be positioned on other parts of the body to sense a physiological signal containing information about patient heart rate or pulse rate. In an example, the ambulatory system 105 may include one or more leadless sensors not being tethered to the AMID 110 via the lead system 108. The leadless ambulatory sensors may be configured to sense a physiological signal and wirelessly communicate with the AMD 110.

The AMD 110 may be configured as a monitoring and diagnostic device. The AMD 110 may include a hermetically sealed can that houses one or more of a sensing circuit, a control circuit, a communication circuit, and a battery, among other components. The sensing circuit may sense a physiological signal, such as by using a physiological sensor or the electrodes associated with the lead system 108. Examples of the physiological signal may include one or more of electrocardiogram, intracardiac electrogram, arrhythmia, heart rate, heart rate variability, intrathoracic impedance, intracardiac impedance, arterial pressure, pulmonary artery pressure, left atrial pressure, right ventricular (RV) pressure, left ventricular (LV) coronary pressure, coronary blood temperature, blood oxygen saturation, one or more heart sounds, intracardiac acceleration, physical activity or exertion level., physiological response to activity, posture, respiration rate, tidal volume, respiratory sounds, body weight, or body temperature.

In an example, the AMD 110 may include a therapy control unit 160 for automatically adjust therapy for treating a medical condition. Examples of the medical condition include cardiac arrhythmias, worsening of a chronic medical condition, such as worsening heart failure (WHF). The therapy control unit 160 may detect an event leading to the medical condition using a signal metric trend generated from one or more physiological signal. The therapy control unit 160 may use the signal metric trend to generate a therapy titration protocol that includes a temporal profile of therapy dosage relative to a target dosage. The target dosage may be adjusted periodically or triggered by an event, based on patient responses. A therapy delivery unit may deliver a therapy according to the therapy titration protocol in response to the detection of the medical condition. In an example, the titration protocol includes a temporal profile of HF drug dosage relative to a target dosage of the HF drug for treating the detected WHF. Examples of the HF drug may include diuretics, ACE inhibitors or Angiotensin II receptor blockers, inotropes, or digoxin, among other medications. In another example, the titration protocol includes adjustment of an electrostimulation therapy, such as stimulation site, stimulation mode, or timing and energy of the stimulation, among others.

The external system 125 may include a dedicated hardware/software system such as a programmer, a remote server-based patient management system, or alternatively a system defined predominantly by software running on a standard personal computer. The external system 125 may manage the patient 102 through the AMD 110 connected to the external system 125 via a communication link 115. This may include, for example, programming the AMD 110 to perform one or more of acquiring physiological data, performing at least one self-diagnostic test (such as for a device operational status), analyzing the physiological data to detect a medical condition, or optionally delivering or adjusting a therapy to the patient 102. Additionally, the external system 125 may receive device data from the AMD 110 via the communication link 115. Examples of the device data received by the external system 125 may include real-time or stored physiological data from the patient 102, diagnostic data such as events of WHF, responses to therapies delivered to the patient 102, or device operational status of the AMD 110 (e.g., battery status and lead impedance). The telemetry link 115 may be an inductive telemetry link, a capacitive telemetry link, or a radio-frequency (RF) telemetry link, or wireless telemetry based on, for example, "strong" Bluetooth or IEEE 802.11 wireless fidelity "WiFi" interfacing standards. Other configurations and combinations of patient data source interfacing are possible.

By way of example and not limitation, the external system 125 may include an external device 120 in proximity of the AMD 110, and a remote device 124 in a location relatively distant from the AMD 110 in communication with the external device 120 via a telecommunication network 122. Examples of the external device 120 may include a programmer device.

The remote device 124 may be configured to evaluate collected patient data and provide alert notifications, among other possible functions. In an example, the remote device 124 may include a centralized server acting as a central hub for collected patient data storage and analysis. The server may be configured as a uni-, multi- or distributed computing and processing system. The remote device 124 may receive patient data from multiple patients including, for example, the patient 102. The patient data may be collected by the AMD 110, among other data acquisition sensors or devices associated with the patient 102. The server may include a memory device to store the patient data in a patient database. The server may include an alert analyzer circuit to evaluate the collected patient data to determine if specific alert condition is satisfied. Satisfaction of the alert condition may trigger a generation of alert notifications. Iii some examples, the alert conditions alternatively or additionally may be evaluated by the AMD 110. By way of example, alert notifications may include a Web page update, phone or pager call, E-mail, SMS, text or "Instant" message, as well as a message to the patient and a simultaneous direct notification to emergency services and to the clinician. Other alert notifications are possible.

The remote device 124 may additionally include one or more locally configured clients or remote clients securely connected over the network 122 to the server. Examples of the clients may include personal desktops, notebook computers, mobile devices, or other computing devices. System users, such as clinicians or other qualified medical specialists, may use the clients to securely access stored patient data assembled in the database in the server, and to select and prioritize patients and alerts for health care provisioning.

The network 122 may provide wired or wireless interconnectivity. In an example, the network 122 may be based on the Transmission Control Protocol/Internet Protocol (TCP/IP) network communication specification, although other types or combinations of networking implementations are possible. Similarly, other network topologies and arrangements are possible.

One or more of the external device 120 or the remote device 124 may output the detected medical events to a system user such as the patient or a clinician, or to a process including, for example, an instance of a computer program executable in a microprocessor. In an example, the process may include an automated generation of recommendations for initiating or titrating a medical therapy or an electrostimulation therapy. In an example, the external device 120 or the remote device 124 may include a respective display unit for displaying the physiological signals, the signal metric trend, or the therapy titration protocol, among other intermediate analyses and computations. Alerts, alarms, emergency calls, or other forms of warnings to signal the detected medical event may also be generated.

Portions of the AMID 110 or the external system 125 may be implemented using hardware, software, firmware, or combinations thereof. Portions of the AMD 110 or the external system 125 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, a memory circuit, a network interface, and various components for interconnecting these components. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
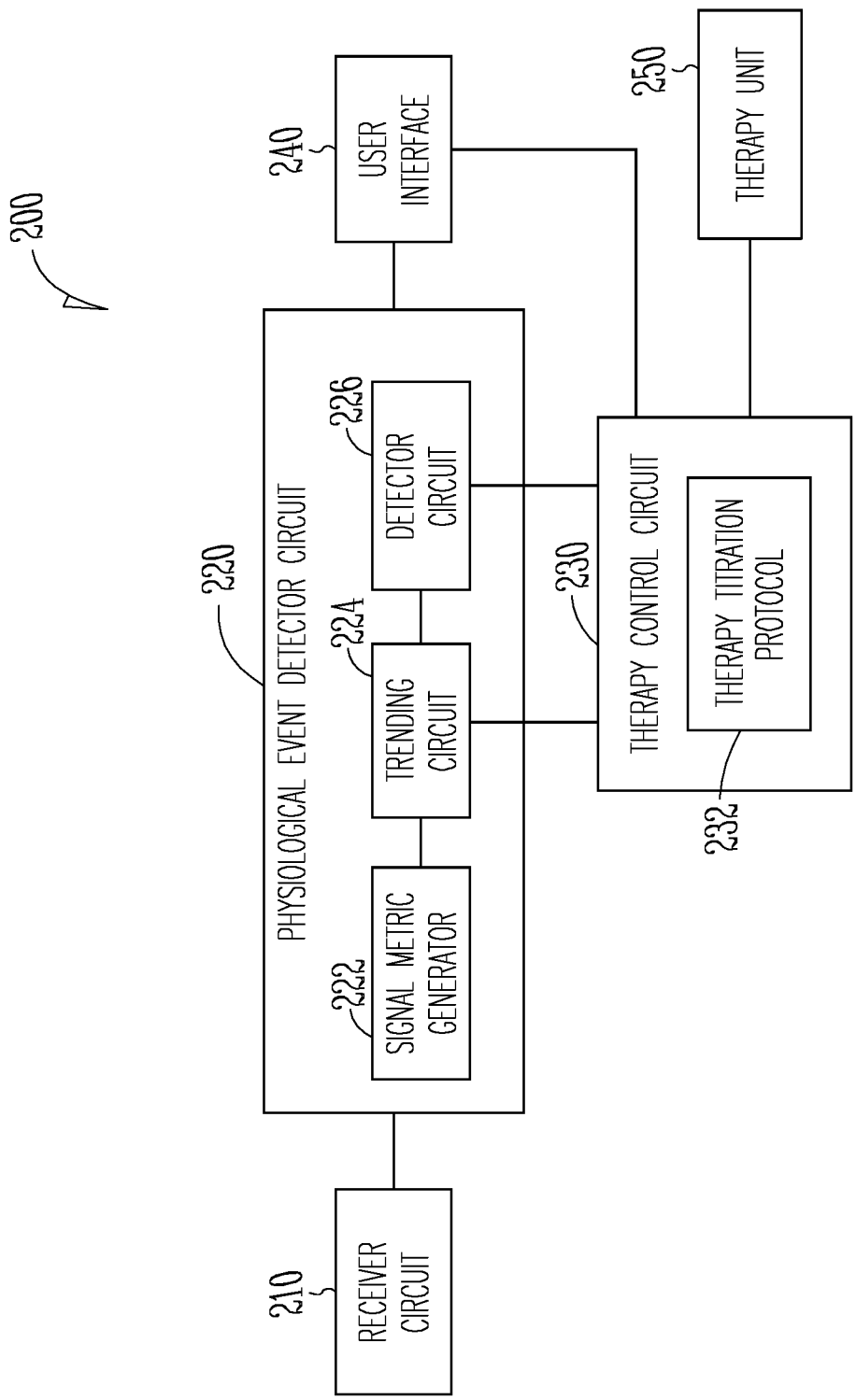
FIG. 2 illustrates generally an example of a patient management system to detect a target physiological event such as worsening heart failure (WHF), and initiate or titrate a therapy.

FIG. 2 illustrates generally an example of a patient management system 200 configured to detect a target physiological event, such as worsening heart failure (WHF), and initiate or titrate a therapy. The patient management system 200 may include one or more of a receiver circuit 210, a physiological event detector circuit 220, a therapy control circuit 230, a user interface 240, and an optional therapy unit 250 for delivering a therapy to treat a disease or to alleviate a medical condition.

At least a portion of the patient management system 200 may be implemented in the AMD 110, the external system 125 such as one or more of the external device 120 or the remote device 124, or distributed between the AMD 110 and the external system 125. In an example, the receiver circuit 210, the physiological event detector circuit 220, and the therapy unit 250 may be implemented in an AMD. In an example, the therapy control circuit 230 and the user interface 240 may be implemented in the external system 125. The external system 125 may determine a therapy titration protocol and present it to a user such as a clinician. Additionally or alternatively, the external system 125 may program the AMD 110 via the communication link 115 according to the therapy titration protocol, and the AMD 110 may deliver a device therapy. In another example, the therapy titration protocol may include a drug dosage profile, and the external system 125 may program a drug delivery system, such as a drug infusion pump, to administer the medication according to the therapy titration protocol automatically or with clinician intervention.

The receiver circuit 210 may receive one or more physiological signals from a patient. In an example, the receiver circuit 210 may be coupled to a sensor circuit that includes a sense amplifier circuit to sense one or more physiological signals from a patient via one or more implantable, wearable, or otherwise ambulatory sensors or electrodes associated with the patient. The sensors may be incorporated into, or otherwise associated with an ambulatory device such as the AMD 110. Examples of the physiological signals may include surface electrocardiography (ECG) sensed from electrodes placed on the body surface, subcutaneous ECG sensed from electrodes placed under the skin, intracardiac electrogram (EGM) sensed from the one or more electrodes on the lead system 108, thoracic or cardiac impedance signal, arterial pressure signal, pulmonary artery pressure signal, left atrial pressure signal, RV pressure signal, LV coronary pressure signal, coronary blood temperature signal, blood oxygen saturation signal, heart sound signal such as sensed by an ambulatory accelerometer or acoustic sensors, physiological response to activity, apnea hypopnea index, one or more respiration signals such as a respiration rate signal or a tidal volume signal, brain natriuretic peptide (BNP), blood panel, sodium and potassium levels, glucose level and other biomarkers and bio-chemical markers, among others. The sensor circuit may include one or more sub-circuits to digitize, filter, or perform other signal conditioning operations on the received physiological signal.

In some examples, the physiological signals may be stored in a data storage device, such as an electronic medical record (EMR) system. The receiver circuit 210 may receive a physiological signal from the data storage device in response to a data retrieval command such as from a system user.

The receiver circuit 210 may also receive patient medical record from a system user, or retrieve the information from the EMR system. The patient medical record may include patient medical history and treatment received, or other contextual information such as time of day, circumstance or daily life contexts, patient environment, economic situation, medical care facilities, or caretaker responsibilities. The patient medical record may also include patient demographic information, such as age, race, gender, cigarette smoking, hypertension, diabetes, or obesity, among others. The patient medical record may be used by the patient management system 200 to detect a target physiological and titrate therapy such as medication dosage.

The physiological event detector circuit 220 may be configured to detect a target physiological event, such as worsening heart failure (WHF). In an example, the physiological event detector circuit 220 can be implemented as a part of a microprocessor circuit in the patient management system 100. The microprocessor circuit can be a dedicated processor such as a digital signal processor, application specific integrated circuit (ASIC), microprocessor, or other type of processor for processing information including heart sounds. Alternatively, the microprocessor circuit can be a general-purpose processor that can receive and execute a set of instructions of performing the functions, methods, or techniques described herein.

In an example such as illustrated in FIG. 2, the physiological event detector circuit 220 may include circuit sets comprising one or more of a signal metric generator circuit 222, a trending circuit 224, and a detector circuit 226. These circuits, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The signal metric generator circuit 222 may generate a signal metric using one or more received physiological signals. The signal metric may include statistical parameters extracted from the sensed physiological signal, such as signal mean, median, or other central tendency measures or a histogram of the signal intensity, among others. In some examples, the signal metric may include morphological parameters extracted from the sensed physiological signal, such as maximum or minimum within a specified time period such as a cardiac cycle, positive or negative slope or higher order statistics, signal power spectral density at a specified frequency range, among other morphological parameters. Depending on the types of the sensed physiological signal, examples of the signal metrics may include thoracic impedance magnitude, intensity of a heart sound component including first (S1), second (S2), third (S3) or fourth (S4), a ratio of a S3 heart sound intensity to a reference heart sound intensity (such as S1 heart sound intensity, heart sound signal energy between R-wave and S2, or heart sound signal energy within a cardiac cycle), a thoracic impedance, a respiration rate, a tidal volume, a ratio a respiration rate to a tidal volume, an activity intensity, or a time duration when the activity intensity is within a specified range or above a specified threshold, among others. In some examples, the signal metrics may include timing parameters, such as one or more HS-based cardiac timing intervals (CTI). The CTI represents electromechanical coupling of the heart, and can be indicative of cardiac functionality and hemodynamic status. Examples of the CTI may include a pre-ejection period (PEP) such as measured between the onset of the QRS to the S1 heart sound, a systolic timing interval (STI) such as measured between the onset of the QRS complex on the ECG to the S2 heart sound, a left-ventricular ejection time (LVET) such as measured as an interval between S1 and S2 heart sounds, or a diastolic timing interval (DTI) such as measured between the S2 heart sound and the onset of the subsequent QRS complex on the ECG, among others. In some examples, the HS metric generator circuit 222 may generate composite measures such as PEP/LVET ratio, STI/DTI ratio, STI/cycle length (CL) ratio, or DTI/CL ratio, among others.

The trending circuit 224 may trend the signal metric over time. The signal metric trend may be formed using multiple measurements of the signal metric during a specified period of time. In an example, the signal metric trend may include a daily trend including daily measurements of a signal metric over a specified number of days. The daily measurement may be determined as a central tendency of a plurality of measurements obtained within a day. In an example, a HS metric may be trended over multiple cardiac cycles or over a period of time. In another example, a thoracic impedance trend may be generated using portions of the received impedance signal during identical phases of a cardiac cycle such as within a certain time window relative to R-wave in a ECG signal), or at identical phases of a respiratory cycle such as within an inspiration phase or an expiration phase of a respiration signal. This may minimize or attenuate the interferences such as due to cardiac or respiratory activities, in the impedance measurements. The thoracic impedance trend may be generated using impedance measurements collected during one or more impedance acquisition and analysis sessions. In an example, an impedance acquisition and analysis session may start between approximately 5 a.m. and 9 a.m. in the morning, and lasts for approximately 2-8 hours. In another example, the impedance acquisition and analysis session may be programmed to exclude certain time periods, such as night time, or when the patient is asleep. The impedance parameter may be determined as a median of multiple impedance measurements acquired during the impedance acquisition and analysis session.

The detector circuit 226 may detect a target physiological event using the signal metric trend. In an example, the detector circuit 226 may use one or more signal metric trends to detect an event leading to WHF. The detector circuit 226 may include a comparator to compare the signal metric trend to a detection threshold to determine an onset or a termination of a WHF event. For example, a WHF event may be detected if S3 intensity ||S3||, such as S3 amplitude or signal energy within the S3 detection window, exceeds an S3 intensity threshold. A louder S3 such as the S3 exceeding an S3 intensity threshold may indicate reduced compliance of the ventricles and deterioration of diastolic function, which may lead to WHF.

In some examples, the signal metric generator 222 may generate a composite signal metric using a combination of signal metrics. The trending circuit 224 may trend the composite signal metric over time, and the detector circuit 226 may detect the target physiological event when the composite signal metric exceeds a detection threshold.

In some examples, the detector circuit 226 may process the signal metric or the composite signal metric to generate a predictor trend indicating temporal changes of the signal metric trend. The temporal change may be calculated using a difference between short-term values and baseline values. In an example, the short-term values may include statistical values such as a central tendency of the measurements of the signal metric within a short-term window of a first plurality of days. The baseline values may include statistical values such as a central tendency of the measurements of the signal metric within a long-term window of a second plurality of days preceding the short-term window in time. In some examples, the predictor trend may be determined using a linear or nonlinear combination of the relative differences between multiple short-term values corresponding to multiple first time windows and multiple baseline values corresponding to multiple second time windows, wherein the differences may be scaled by respective weight factors which may be based on timing information associated with corresponding multiple short-term window, such as described by Thakur et al., in U.S. Patent Publication No. 2017/0095160, entitled "PREDICTIONS OF WORSENING HEART FAILURE", which is herein incorporated by reference in its entirety.

The therapy control circuit 230 may be coupled to the trending circuit 224 and the detector circuit 226, and generate a therapy titration protocol 232 using the signal metric trend from the trending circuit 224 and the information about the detected physiological event from the detector circuit 226. The therapy control circuit 230 may dynamically up-titrate or down-titrate the therapy dosage in accordance with the growth trend or a decay trend of the signal metric or the composite signal metric. Up-titration of therapy dosage refers to an increase in quantity or frequency of medication dose at specified time or manner, an increase in electrostimulation intensity or duration at specified time or manner, or addition of a new medication or device therapy such as to boost therapeutic effect at specified time or manner. Down-titration of therapy dosage refers to a decrease in quantity or frequency of medication dose at specified time or manner, a decrease in electrostimulation intensity or duration at specified time or manner, or cutback of a present medication or device therapy at specified time or manner. Timing of the therapy titration may be based on the timing of onset or termination of the detected physiological event. In some examples, up- or down-titration of therapy dosage may be triggered by one or more medical events. For example, a down-titration of diuretic may be initiated if the patient is over diuresis, or an up-titration of diuretic may be initiated if the patient undergoes a surgery that requires intravenous fluid infusion.

The therapy titration protocol 232 may include a temporal profile of therapy dosage. The therapy dosage represents individualized quantity and frequency of one or more therapeutic agents (e.g., medications or electrostimulation) relative to a target dosage. The target dosage represents a baseline therapeutic agent dosage administered to patients of similar medical conditions. The target dosage may be based on safety and efficacy information about the therapeutic agent, and provided to the patient management system 200 by a system user such as via the user interface 240. Examples of therapy titration protocol 232 are discussed below, such as with reference to FIGS. 3-5.

The therapy unit 250 may be configured to deliver a therapy to the patient according to the therapy titration protocol 232 in response to the detection of WHF event. In an example, the therapy unit 250 may include an electrostimulator circuit configured to generate and deliver electrostimulation therapy to treat a medical condition such as WHF in response to a detection of an event leading to WHF. Examples of the electrostimulation may include cardiac pacing therapy, cardioversion therapy, defibrillation therapy, or electrostimulation of non-cardiac tissues such as nerve tissues, muscle tissues, among other excitable tissues of the patient. The therapy control circuit 230 may generate a HF electrostimulation protocol including the stimulation site, stimulation mode, or stimulation timing and stimulation energy, among other parameters. The stimulation mode may include cardiac resynchronizati on therapy (CRT), which may be a biventricular (BiV) pacing of both left and right ventricles, or synchronized left ventricle (LV)-only pacing. The stimulation mode may also include single site pacing of only one site of a heart chamber (e.g., the left ventricle) within a cardiac cycle, or multisite pacing (MSP) of two or more sites of a heart chamber within the same cardiac cycle. In an example, the MSP may be delivered within the LV. Two or more LV sites may be selected for pacing via multiple LV electrodes. Stimulation strength parameters controls the amount of energy delivered to the pacing site. Examples of the stimulation strength parameters may include pulse width, pulse amplitude, frequency, duty cycle, or stimulation duration. Stimulation timing parameters determine the timing and sequence of electrostimulation pulses, and may have an impact on therapy efficacy and hemodynamic outcome. The therapy unit 250 may deliver electrostimulation according to the electrostimulation protocol, in response to the detector circuit 226 detecting the WHF event.

In another example, the therapy unit 250 may include a drug delivery system such as a drug infusion pump configured to administer one or more medication to treat a medical condition such as WHF. Examples of the HF drug may include diuretics, ACE inhibitors or Angiotensin II receptor blockers, inotropes, or digoxin, among other medications. The therapy control circuit 230 may generate a HF therapy titration protocol including a temporal profile of HF drug dosage relative to a target dosage. The therapy unit 250 may automatically, or with clinician intervention, administer the medication according to the temporal profile of HF drug dosage, in response to the detector circuit 226 detecting the WHF event.

The user interface 240 may include an input unit and an output unit. In an example, at least a portion of the user interface 240 may be implemented in the external system 125. The input unit may receive user input that controls the WHF detection or therapy titration protocol generation. In an example, the input unit may receive user input of target dosage, which represents a baseline therapeutic agent dosage administered to patients of similar medical conditions. The user input may receive user confirmation, rejection, or otherwise modification of therapy titration recommendations. The input unit may include an input device such as a keyboard, on-screen keyboard, mouse, trackball, touchpad, touch-screen, or other pointing or navigating devices.

The output unit may include circuitry configured to generate a human-perceptible notification of the detected target physiological event. The output circuit may be coupled to a display for displaying the received physiological signals, trends of the signal metrics or the composite signal metric, the therapy titration protocol, or a therapy titration recommendation, among other intermediate measurements or computations. The output circuit 230 may be coupled to a printer for printing hard copies of information about the event detection and therapy titration protocol. The information may be presented in a table, a chart, a diagram, or any other types of textual, tabular, or graphical presentation formats. The presentation of the output information may include audio or other media format. In an example, the output unit may generate alerts, alarms, emergency calls, or other forms of warnings to signal the system user about the detected target physiological event, such as a WHF event.

Although the discussion of therapy titration protocol throughout this document focuses on the therapy for WHF, this is meant only by way of example and not limitation. Systems, devices, and methods discussed in this document may also be suitable for detecting various sorts of chronic diseases including, for example, coronary artery disease, chronic obstructive pulmonary disease, or chronic kidney disease, among many others.

FIG. 3 illustrates generally an example of a therapy titration system 300 configured to generate a therapy titration protocol for treating a medical condition. The therapy titration system 300 is an embodiment of at least part the patient management system 200. The therapy titration system 300 may include a therapy control circuit 330 coupled to the event detector 226, the trending circuit 224, and the receiver circuit 210 as discussed above with reference to FIG. 2.

The therapy control circuit 330, which is an embodiment of the therapy control circuit 230, may be implemented as a part of a microprocessor circuit, which may be a dedicated processor or a general-purpose processor that may receive and execute a set of instructions of performing the functions, methods, or techniques described herein. Alternatively, the therapy control circuit 330 may include circuit sets comprising one or more other circuits or sub-circuits, such as a titration timing circuit 332, an up/down titration circuit 334, a target dosage adjustment circuit 336, and a therapy titration protocol generator 338. These circuits may, alone or in combination, perform the functions, methods, or techniques described herein.

The titration timing circuit 332 may be coupled to the event detector 226 and the trending circuit 224, and determine timings of dosage titration using one or more of information about the detection of the physiological events provided by the event detector 226, or a signal metric trend or a trend of a composite signal metric provided by the trending circuit 224. The timings of the dosage titration may include beginning and end of up-titration, or beginning and end of down-titration of a therapy dosage. For example, the therapy control circuit 330 may up-titrate the therapy dosage when the signal metric trend exceeds an onset threshold, indicating an onset of a target physiological event. The therapy control circuit 330 may down-titrate the therapy dosage at the time when the signal metric trend falls below a reset threshold, indicating an end of the detected target physiological event. The onset threshold may be the same as or different from the reset threshold. In some examples, the titration timing circuit 332 may initiate delayed up-titration of therapy dosage at a latency subsequent to the signal metric trend crossing the onset threshold. Similarly, the titration timing circuit 332 may initiate delayed down-titration of therapy dosage at a latency subsequent to the signal metric trend crossing the reset threshold. The delayed titration may help avoid therapy titration inappropriately triggered by temporary fluctuation of the signal metric trend, which does not represent a sustained worsening or improvement of the underlying condition. In an example, the therapy control circuit 330 may up-titrate the therapy dosage when the signal metric trend exceeds the detection threshold and maintains a growth trend above the onset threshold. In another example, the therapy control circuit 330 may down-titrate the therapy dosage when the signal metric trend indicates lack of a sustained worsening of the physiological condition, such as when then signal metric trend falls below a detection threshold and maintains a decay trend below the reset threshold.

The up/down titration circuit 334 may be coupled to the trending circuit 224, and determine one or more of a direction of titration (e.g., up-titration or down-titration), amount of titration, or a mode of titration of therapy dosage. The amount of titration refers to a change in quantify or in frequency of drug administration or electrostimulation energy relative a target dosage. The up/down titration circuit 334 may confine the up- and down-titration within a bounded range in reference to the target dosage. For example, the up-titration of the therapy dosage may be no higher than a specific upper bound dosage, and the down-titration of the therapy dosage may he no lower than the target dosage. The mode of titration refers to a rate of change of therapy dosage, or a temporal profile of the change of therapy dosage. Examples of the titration mode may include linear, piece-wise linear, step, exponential, parabolic, or other non-linear functions. Examples of titration of therapy dosage, including timing, direction, amount, or mode of titration, are discussed below, such as with reference to FIGS. 4A-B.

The target dosage adjustment circuit 336 may be coupled to the receiver circuit 210 and the trending circuit 224, and adjust the target dosage periodically, or in response to a trigger event or user command. In an example, the target dosage may adjusted when the signal metric trend satisfies a specific condition. The receiver circuit 210 may receive, such as from a clinician, a target dosage representing a baseline therapeutic agent dosage administered to patients of similar medical conditions. The target dosage adjustment circuit 336 may adjust the target dosage using a comparison of the portion of the temporal profile of therapy dosage representing and historical therapy dosage applied to the patient (such as provided by the therapy titration protocol generator 338) to the present target dosage. Unlike the up/down titration of the therapy dosage that determines instantaneous or short-term therapy dose, the target dosage adjustment may provide an individualized long-term reference dosage that may be used to guide the up- or down-titration strategy.

The target dosage adjustment circuit 336 may include a timer circuit to determine a time duration when the target dosage satisfies a specific condition relative to the target dosage. In an example, if the temporal profile of therapy dosage is above the target dosage for a specified time period, which may indicate that the patient is effectively treated by, and consistently tolerated to, a higher dose above the target dosage, then the target dosage adjustment circuit 336 may increase the target dosage. The target dosage may be increased to a level based on the temporal profile of therapy dosage during the specified time period. In an example, the target dosage may be increased to a level corresponding to a lowest therapy dosage achieved during the specified period.

In another example, the target dosage adjustment circuit 336 may decrease the target dosage through a testing procedure. The testing procedure may involve temporary down-titration of the therapy dosage to a sub-target level that is lower than the present target dosage. Patient response to the therapy with the sub-target dosage treatment may be evaluated within an assessment time period. The patient response may include subjective or objective measures, such as patient signs, symptoms, physiological or functional parameters, change of daily activities or routines, among others. If the patient experiences no worsening of the physiological or functional conditions during the assessment period, then the target dosage adjustment circuit 336 may decrease the target dosage to a level corresponding to the down-titrated therapy dosage. In an example, the patient response may be assessed using a signal metric trend, or a composite signal metric trend, such as generated by the trending circuit 224 from the physiological information acquired during the testing procedure. The target dosage adjustment circuit 336 may decrease the target dosage if the signal metric trend remains within a specific range indicating no worsening of the physiological condition during the assessment period.

Examples of target dosage adjustment are discussed below, such as with reference to FIGS. 5A-B.

The therapy titration protocol generator 338 may generate a therapy titration protocol that defines a set of instructions to assist a clinician or guide a therapy unit in adjusting patient therapy under specific conditions. As illustrated in FIG. 3, the titration protocol may be generated using one or more titration parameters, such as titration timing determined by the titration timing circuit 332, titration direction and amount or mode of titration determined by the up/down titration circuit 334, and the target dosage determined by the target dosage adjustment circuit 336. The therapy titration protocol may include a temporal profile of therapy dosage indicating therapy dosage at different time. The generated therapy titration protocol may be presented to a user such as a clinician via a display of the user interface 240, or be used to guide therapy delivery such as via the therapy unit 250. Portions of the generated therapy titration protocol may be used to adjust the target dosage by the target dosage adjustment circuit 336.

Figure 4A:
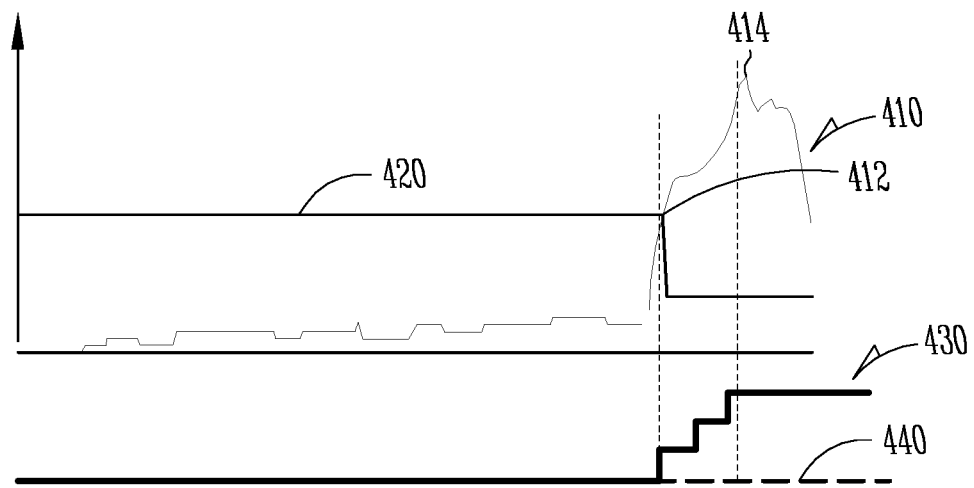
FIGS. 4A-B illustrate examples of a therapy titration protocol determined using a signal metric trend and a target dosage.
Figure 4B:
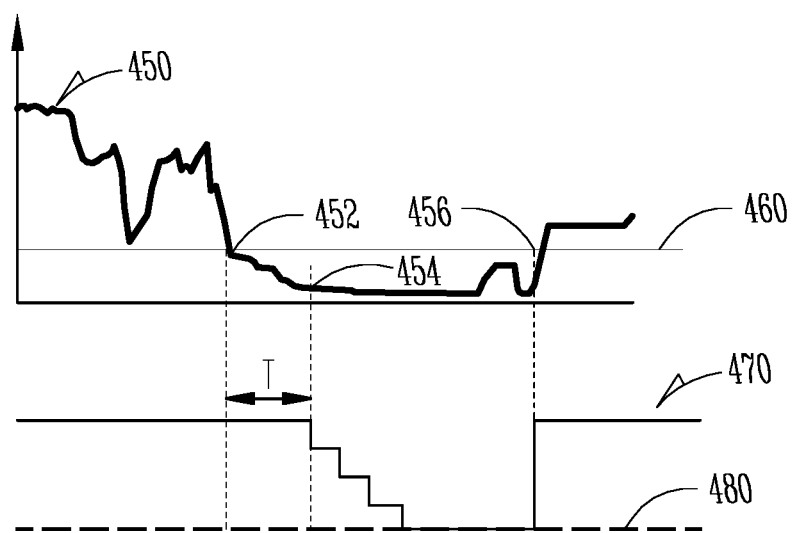

FIGS. 4A-B illustrate examples of a therapy titration protocol determined using a signal metric trend and a target dosage. The therapy titration protocol may be determined using the therapy control circuit 230 or the therapy control circuit 330. The therapy titration protocol includes a set of instructions for adjusting patient therapy under specific conditions. A temporal profile of therapy dosage may be generated from the set of instructions. The temporal profile of therapy dosage represents individualized quantity and frequency of one or more therapeutic agents relative to the target dosage.

FIG. 4A illustrates an example of a therapy dosage profile 430 including a portion of dosage up-titration. The up-titration corresponds in time to temporal changes of a signal metric trend 410, which may be generated by the signal metric generator 222 and the trending circuit 224 from one or more physiological signals. As illustrated in FIG. 4A, the therapy dosage starts at a level corresponding to the target dosage 440. As the signal metric trend 410 ramps up over time and crosses an onset threshold 420 at 412, the detector circuit 226 detects an onset of physiological event (e.g., a WHF event). Thereafter, the onset threshold 420 is decreased to a reset threshold for detecting a termination of the detected event.

In response to the detection at 412, an up-titration of therapy dosage is initiated. In some examples, the up-titration of therapy dosage may be delayed until after a specific latency period following the detection at 412. The up-titration continues as long as the signal metric trend 410 maintains a growth trend until it reaches a peak 414. By way of example and not limitation, corresponding to the growth trend of the signal metric trend between 412 and 414, the up-titration may follow a step function. The amount of up-titration or the time interval at each step may be constant or variable across the steps, or may be user programmable. In an example, the time interval at each step is a constant, such as one week, or a specified number of days. Following the peak 414, the signal metric trend 410 decreases. Accordingly, the step-wise up-titration process stops, and the therapy dosage is maintained at its present level. Because the signal metric trend 410 is still above the detection threshold 420 (that is, the detected event has not terminated), no down-titration process is initiated in this example.

FIG. 4B illustrates an example of therapy dosage profile 470 including a portion of dosage down-titration. The dosage down-titration corresponds to temporal changes of a signal metric trend 450, which may be generated by the signal metric generator 222 and the trending circuit 224 from one or more physiological signals. As illustrated in FIG. 413, the signal metric trend 450 begins at a level above a detection threshold 460, indicating an on-going physiological event (e.g., WHF). Correspondingly, the therapy dosage begins at a level higher than the target dosage 480. As the signal metric trend 450 ramps down over time and crosses the detection threshold 460 at 452, the detector circuit 226 may detect a termination of the physiological event. The therapy dosage, however, may be maintained for a latency period (T). The latency period (T) may be user programmable, or determined based on the signal metric trend 450 crosses a threshold lower than the detection threshold 460. After the latency period T, down-titration may be initiated at 454 such as via the titration timing circuit 332. The delayed down-titration, as illustrated in FIG. 4B, may be beneficial in circumstances where the detection of physiological event termination (e.g., detection threshold crossing) is followed by fluctuations of the signal metric trend, which may not represent a steady decrease of the signal metric trend and a patient condition under control. Maintaining the therapy dosage for an extended time period (e.g., T) may ensure sufficient therapy prior to establishing a high confidence that the patient condition is under control or has improved over time, at which point a therapy down-titration may be initiated. By way of example and not limitation, corresponding to the decay trend of the signal metric trend 450 between 452 and 454, and the sustained low signal metric level beyond 454, the down-titration may follow a step function. The step-wise down-titration may have a constant or variable amount of down-titration and time interval at each step. The down-titration continues until the therapy dosage reaches the target dosage. The therapy dosage may be maintained at the target dosage level until the signal metric trend 450 ramps up and exceeds the detection threshold at 456, at which the detector circuit 226 may detect an onset of another physiological event. In response to the event detection at 456, the therapy dosage may be increased from its present level (corresponding to the target dosage) to a specific elevated dosage. Alternatively, the therapy dosage may follow a step-wise up-titration similar to the therapy dosage profile 430 in FIG. 4A.

Figure 5A:
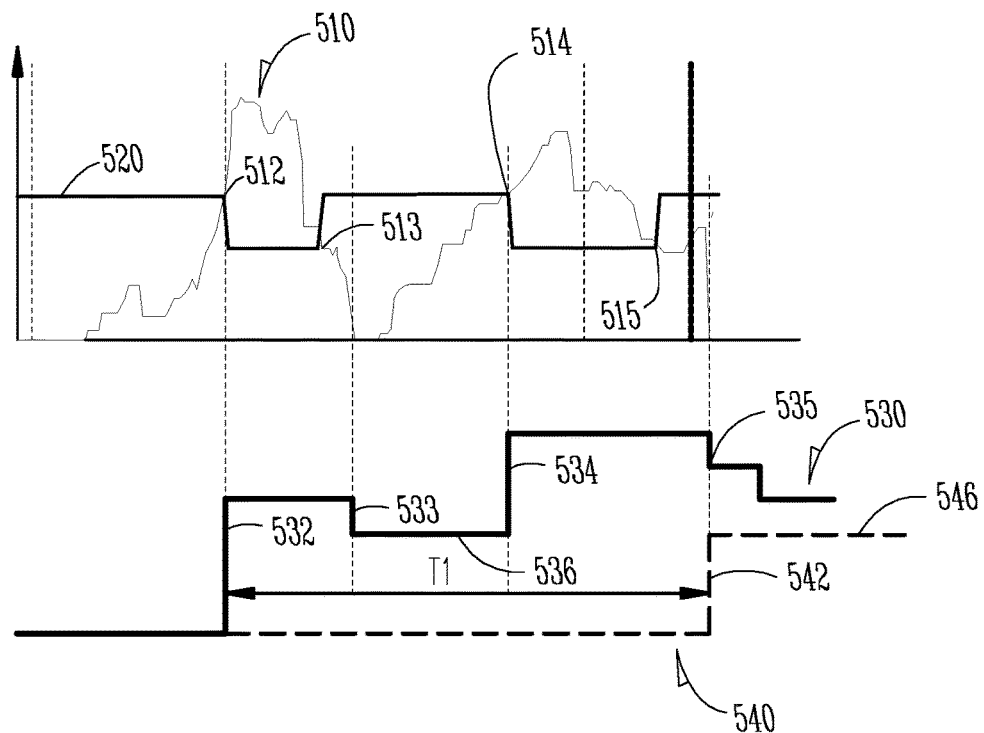
FIGS. 5A-B illustrate examples of target dosage adjustment using a comparison of a temporal profile of therapy dosage and a target dosage.
Figure 5B:
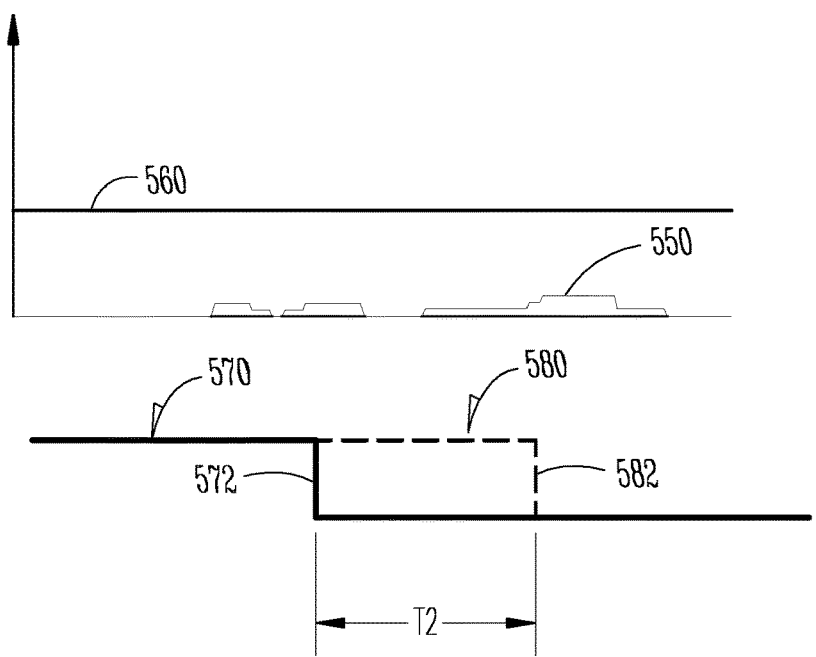

FIGS. 5A-B illustrate examples of target dosage adjustment using a comparison of a temporal profile of therapy dosage and a target dosage. The adjusted target dosage may be generated using the target dosage adjustment circuit 336 as illustrated in FIG. 3.

FIG. 5A illustrates an example of target dosage profile 540 that includes an increase in the target dosage. Also illustrated in FIG. 5A is a signal metric trend 510 and a therapy dosage profile 530 that includes portions of up-titration and down-titration of therapy dosage corresponding in time to the signal metric trend 510 and the detection of the onset and the termination of the physiological event, similar to the previous discussion with reference to FIG. 4A. As illustrated in FIG. 5A, the portions of growth trends of the signal metric trend 510 and the threshold crossings at 512 and 514 each may trigger respective up-titrations 532 and 534 of the therapy dosage. The portions of decay trends of the signal metric trend 510 and the threshold crossings at 513 and 515 each may trigger respective delayed down-titrations 533 and 535 of the therapy dosage following respective latency periods after the threshold crossings at 513 and 515.

The dosage adjustment circuit 336 may monitor the therapy dosage 530, compare it to the target dosage 540, and count time elapsed when the target dosage satisfies a specific condition, such as being above the target dosage. In the example illustrated in FIG. 5A, the up-titration at 532 results in a therapy dosage above the target dosage. Following a decay trend from 513 and a brief period of meandering at a low signal metric level, the signal metric trend 510 bounces back and demonstrates a growth trend. Corresponding to such a pattern of the signal metric trend, the down-titration at 533 does not sustain long enough, and the signal metric trend remains at the level 536 above the target dosage. From the up-titration at 532, the time elapsed (T1) when the therapy dosage stays above the target dosage exceeds a duration threshold, and the target dosage adjustment circuit 336 may increase the target dosage at 542 to a level based on the temporal profile of therapy dosage during the specified time period. In an example, the target dosage may he increased to a level 546 corresponding to a lowest therapy dosage 536 achieved during the time period T1. From that point on, therapy dosage titration may be determined using the signal metric trend 510 and the new, increased target dosage unless further adjustment of target dosage is initiated.

FIG. 5B illustrates an example of target dosage profile 580 that includes a decrease in the target dosage. Also illustrated in FIG. 5B is a signal metric trend 550, and a therapy dosage profile 570 that starts at a level corresponding to a target dosage 580. In FIG. 5B, the signal metric trend 550 is below the threshold 560 for a prolonged time period, during which the therapy dosage maintains at the target dosage 580. Patient physiological and functional responses may be monitored while the patient receives treatment with the target dosage. If no worsening of the physiological or functional condition is indicated for a sustained period of time, a testing procedure may be triggered at 572 to temporarily down-titrate the therapy dosage. The amount of down-titration may be user programmable. Evaluation of patient physiological or functional responses to the temporarily down-titrated therapy dosage may be continued over a time period T2. In some examples, patient physiological or functional responses may be evaluated using the signal metric or the composite signal metric acquired during the down-titrated therapy procedure. If the patient demonstrates no worsening of the physiological or functional conditions during the assessment period, or if the signal metric trend 550 remains within a specific range indicating patient tolerance and therapy efficacy during the assessment period, then at 582, the target dosage may be decreased to a level corresponding to the down-titrated therapy dosage. From that point on, therapy dosage titration may be determined using the signal metric trend 550 and the new, decreased target dosage unless further adjustment of target dosage is initiated.

Figure 6:
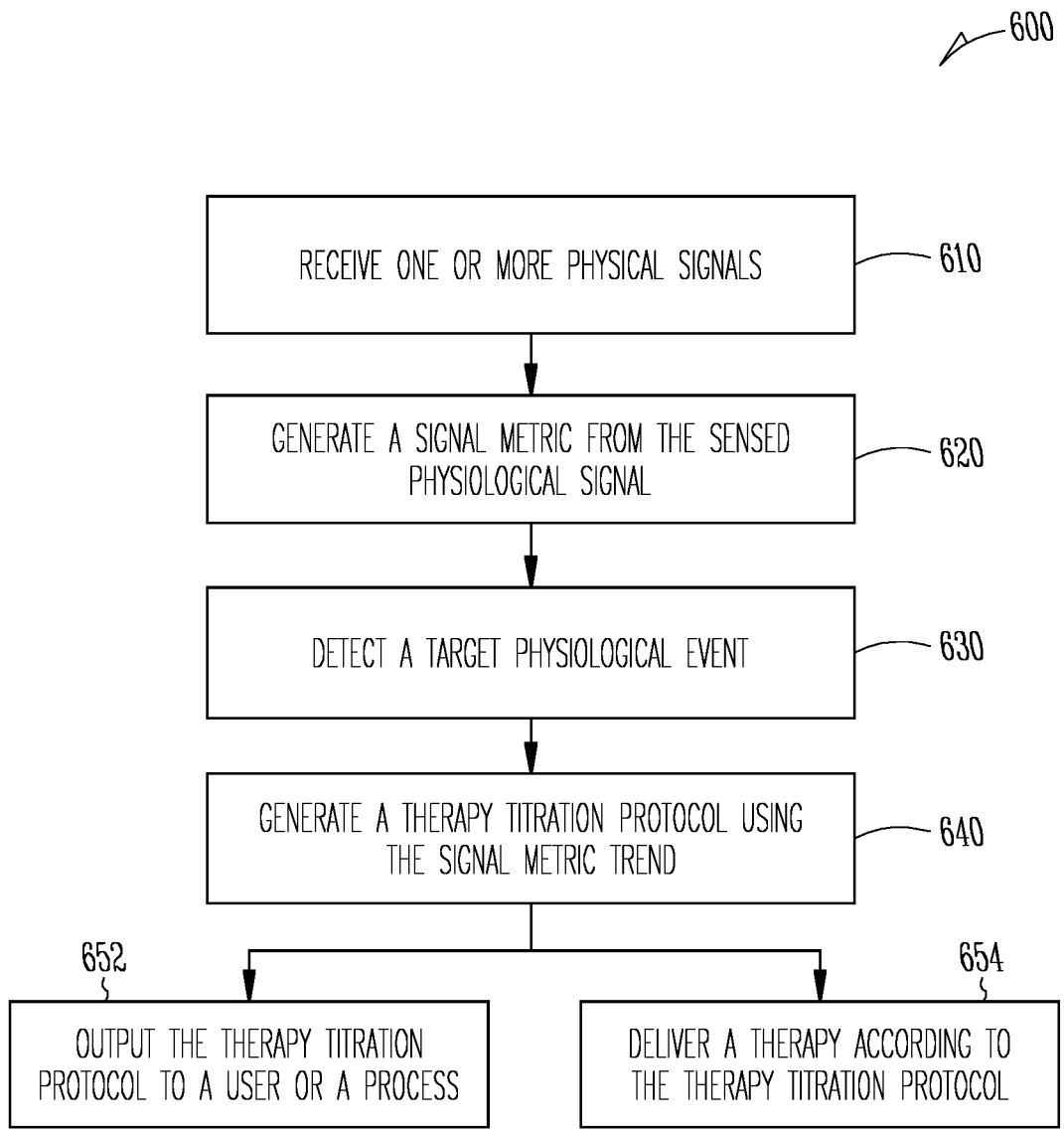
FIG. 6 illustrates generally an example of a method for adjusting a therapy in a patient.

FIG. 6 illustrates generally an example of a method 600 for adjusting a therapy in a patient using a medical system. The method 600 may be implemented and executed in an ambulatory medical device such as an implantable or wearable medical device, or in a remote patient management system. In an example, the method 600 may be implemented in, and executed by, the AMD 110, one or more devices in the external system 125, or the patient management system 200 or the therapy titration system 300.

The method 600 begins at 610, where one or more physiological signals may be received, such as via receiver circuit 210. The physiological signals may be sensed from a patient via one or more implantable, wearable, or otherwise ambulatory sensors or electrodes associated with the patient. Alternatively, the physiological signals may be received from a data storage device in response to a data retrieval command such as from a system user. Examples of the physiological signals may include ECG, intracardiac EGM, thoracic or cardiac impedance signal, arterial pressure signal or cardiac pressure signal, coronary blood temperature signal, blood oxygen saturation signal, heart sound signal such as sensed by an ambulatory accelerometer or acoustic sensors, physiological response to activity, apnea hypopnea index, one or more respiration signals such as a respiration rate signal or a tidal volume signal, brain natriuretic peptide (BNP), blood panel, sodium and potassium levels, glucose level and other biomarkers and bio-chemical markers, among others.

At 620, a signal metric from the sensed one or more physiological signals, such as via the signal metric generator circuit 222. The signal metric may include statistical parameters, morphological parameters, or timing parameters, among others. In some examples, the signal metric may include a composite signal metric using a combination of signal metrics. The signal metric may be trended over time, such as by using the trending circuit 224. In an example, the signal metric trend may include a daily trend including daily measurements of a signal metric over a specified number of days. The daily measurement may be determined as a central tendency of a plurality of measurements obtained within a day.

At 630, a target physiological event may be detected using the signal metric trend, such as via the detector circuit 226. An example of the target physiological event is an event leading to worsening heart failure (WHF), such as a heart failure decompensation event. The signal metric trend, or the composite signal metric trend, may be compared to a detection threshold to determine an onset or a termination of a WHF event. In an example, a WHF event may be detected if S3 intensity ‖S3‖, such as S3 amplitude or signal energy within the S3 detection window, exceeds an S3 intensity threshold. A louder S3 such as the ‖S3‖ exceeding an S3 intensity threshold may indicate reduced compliance of the ventricles and deterioration of diastolic function, which may lead to WHF. In some examples, a predictor trend indicating temporal changes of the signal metric trend may be calculated using a difference between short-term values and baseline values of a signal metric or a composite signal metric. The baseline values may include statistical values such as a central tendency of the measurements of the signal metric within a long-term window preceding a short-term window from which the short-term values are computed. A WHF event is detected if the predictor trend exceeds a threshold.

At 640, a therapy titration protocol may be generated using the signal metric trend and the information about the detected physiological event, such as via the therapy control circuit 230. The therapy titration protocol may include a temporal profile of therapy dosage. The temporal profile of therapy dosage may include one or more of an up-titration or a down-titration of therapy dosage corresponding to the growth trend or a decay trend of the signal metric or the composite signal metric. Up-titration of therapy dosage refers to an increase in quantity or frequency of medication dose at specified time or manner, or an increase in electrostimulation intensity or duration at specified time or manner. Down-titration of therapy dosage refers to a decrease in quantity or frequency of medication dose at specified time or manner, or a decrease in electrostimulation intensity or duration at specified time or manner. Timing of the therapy titration may be based on the timing of onset or termination of the detected physiological event. Examples of methods for titrating therapy are discussed below, such as with reference to FIG. 7.

The therapy dosage represents individualized quantity and frequency of one or more therapeutic agents relative to a target dosage. The target dosage represents baseline therapeutic agent dosage administered to patients of similar medical conditions. The target dosage may be based on safety and efficacy information about the therapeutic agent. Unlike the up/down titration of the therapy dosage which determines instantaneous or short-term therapy dose, the target dosage adjustment may provide an individualized long-term reference dosage, and may be used to guide the up- or down-titration strategy. The target dosage may be adjusted based on patient response. Examples of methods of adjusting target dosage are discussed below, such as with reference to FIG. 7.

The therapy titration protocol may be output to a user (e.g., a clinician) or a process at 652, such as being displayed on a display of the user interface 240. The received physiological signals, trends of the signal metrics or the composite signal metric, or therapy titration recommendations, among other intermediate measurements or computations, may also be displayed. Additionally or alternatively, at 654, therapies may be delivered according to the therapy titration protocol, such as via the therapy circuit 260. Examples of the therapy may include electrostimulation therapy delivered to the heart, a nerve tissue, other target tissues, a cardioversion therapy, a defibrillation therapy, or drug therapy including delivering drug to a tissue or organ. Electrostimulation therapy may be delivered according to a HF therapy titration protocol that specifies stimulation site, stimulation mode, or stimulation timing and stimulation energy, among other parameters. In some examples, at 654, the therapy may include drug therapy, such as delivered via a drug infusion pump to treat WHF. Examples of the HF drug may include diuretics, ACE inhibitors or Angiotensin II receptor blockers, inotropes, or digoxin, among other medications. Medication may be automatically, or with a clinician intervention, administered according to the temporal profile of HF drug dosage, in response to the detected WHF event.

Figure 7:
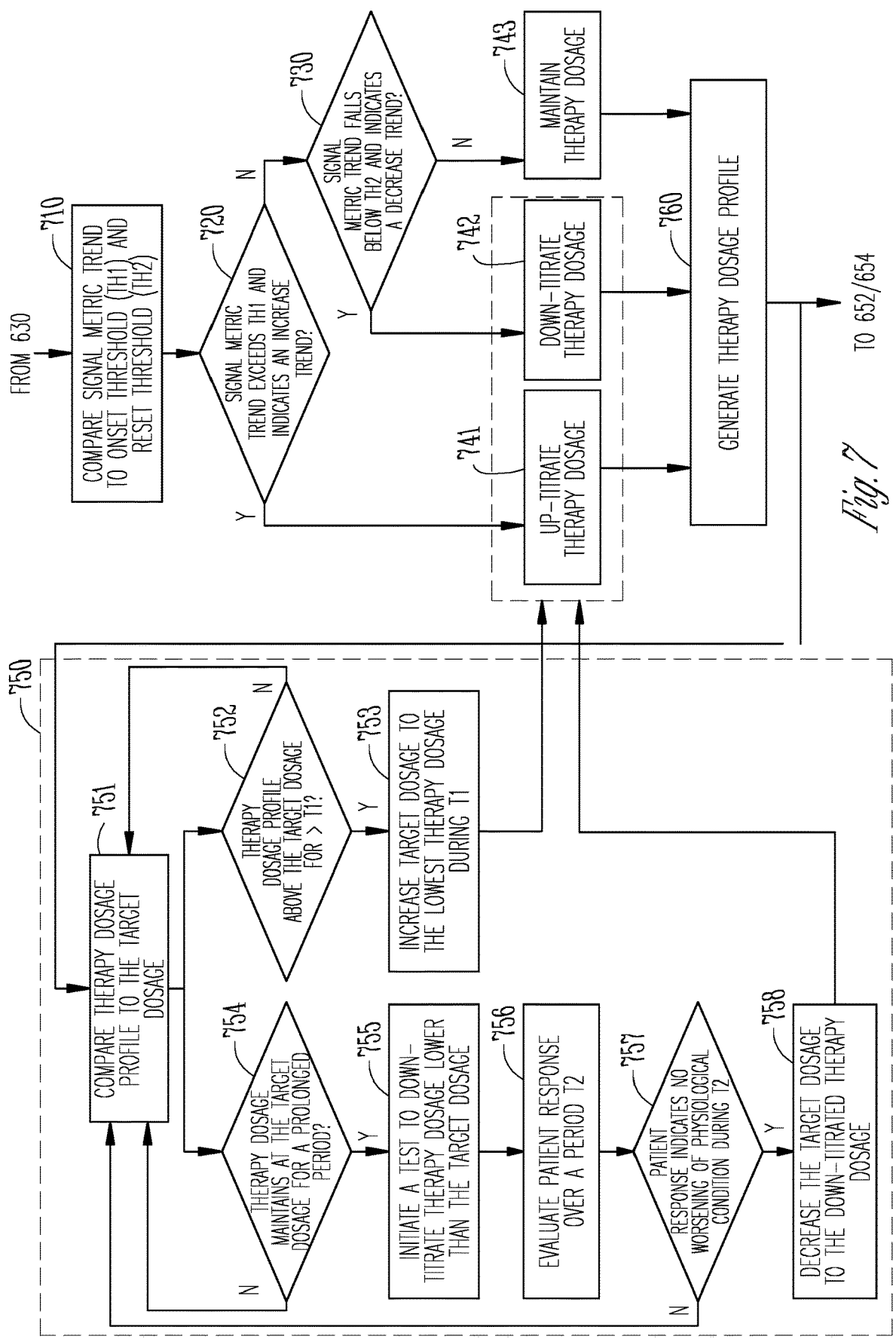
FIG. 7 illustrates generally an example of a method for generating a therapy dosage profile to guide treatment of a medical condition.

FIG. 7 illustrates generally an example of a method 700 for generating a therapy dosage profile that may be used to guide treatment of a medical condition such as WHF. The method 700 may be an embodiment of a portion of the method 600, such as step 640 of generating a therapy titration protocol. The method 700 may be implemented in, and executed by the therapy titration system 300, and include a set of instructions for adjusting patient therapy under specific conditions.

The method 700 begins at 710 to compare the signal metric trend or the composite signal metric trend generated 620 to one or more detection thresholds, such as a WHF onset threshold $TH_1$ or a WHF reset threshold $TH_2$. By way of example and not limitation, an increase trend of the signal metric indicates sustained worsening of heart failure status, and a decrease trend of the signal metric indicates lack of sustained worsening of heart failure status (e.g., a heart failure status that is under control or has improved over time). :A beginning of the WHF event is detected when the signal metric trend increases and exceeds the onset threshold $TH_1$. An end of the detected WHF event is detected when the signal metric trend decreases and falls below the reset threshold $TH_2$. The onset threshold $TH_1$ may be the same as, or different from, the reset threshold $TH_2$.

The threshold crossing may trigger the dosage titration, such as via the titration timing circuit 332. At 720, if the signal metric trend exceeds $TH_1$, and if the signal metric maintains a growth trend above the detection threshold $TH_1$, then an up-titration of therapy dosage may be carried out at 741 to alleviate the worsening of heart failure. If no threshold crossing of $TH_1$ is detected, the signal metric trend may be compared to the reset threshold $TH_2$. At 730, if the signal metric trend falls below the reset threshold $TH_2$, and if the signal metric maintains a decay trend below the detection threshold $TH_2$, then a down-titration of therapy dosage may be performed at 742 to adapt to the heart failure status that is under control or has improved over time with the present therapy. If no threshold crossing of $TH_1$ or $TH_2$ is detected, or if the threshold crossing of $TH_1$ is not accompanied by a maintained growth trend, or if the threshold crossing of $TH_2$ is not accompanied by a maintained decay trend, then at 743, the therapy dosage may be maintained at its present level without titration.

In some examples, the up-titration of therapy dosage at 741 or the down-titration of therapy dosage at 742 may be initiated at a latency after the signal metric trend crosses the respective onset threshold $TH_1$ or the reset threshold $TH_2$. Such delayed titration may be beneficial in circumstances where the detection of physiological event termination (e.g., detection threshold crossing) is followed by fluctuations of the signal metric trend. Maintaining the therapy dosage for an extended time period may ensure sufficient therapy prior to establishing a high confidence that the patient condition is under control or has improved over time with the present therapy, at which point the down-titration of therapy may be initiated.

The up-titration at 741 and the down-titration 742 of therapy dosage may be confined within a bounded range with respect to a target dosage. For example, the up-titration of the therapy dosage is no higher than a specific upper bound dosage, or the down-titration of the therapy dosage is no lower than the target dosage. The amount of up- or down-titration corresponds to a change in quantify or in frequency of drug administration or electrostimulation energy relative a target dosage. As illustrated in FIG.7, the method 700 includes a method 750 for automatic adjustment of the target dosage. The method 750 may be implemented in, and executed by, the target dosage adjustment circuit 336. The therapy dosage profile, including historical dosage, may be compared to the present target dosage at 751. If it is determined at 752 that the therapy dosage is above the present target dosage for at least a sustained time period of Ti, then the patient is effectively treated by, and consistently tolerated to, the higher dose above the target dosage. Accordingly, at 753, the target dosage may be increased to a level based on the temporal profile of therapy dosage during the specified time period. In an example, the target dosage may be increased to a level corresponding to a lowest therapy dosage achieved during the specified period, such as the example illustrated in FIG. 5A.

At 754, if it is determined that the therapy dosage maintains at the present target dosage for a prolonged time period, such as approximately 60-120 days, then a testing procedure may be initiated at 755 to attempt to decrease the target dosage. The testing procedure may involve temporary down-titrating the therapy dosage to a level lower than the present target dosage, such as the example illustrated in FIG. 5B. At 756, patient response to the therapy with the sub-target dosage treatment may be evaluated within an assessment time period T2. The patient response may be assessed using subjective or objective measures, such as patient signs, symptoms, physiological or functional parameters, change of daily activities or routines, among others. If at 757 the patient demonstrates no worsening of the physiological or functional conditions during the assessment period T2, or if the signal metric trend remains within a specific range indicating patient tolerance and therapy efficacy during the assessment period T2, then at 758 the target dosage may be decreased to a level corresponding to the down-titrated therapy dosage. If at 757 the patient demonstrates worsening of the physiological or functional conditions during the assessment period T2, then the target dosage is maintained at its present level, and the target dosage assessment may continue at 751.

The adjusted target dosage, such as an increase of the target dosage as determined at 753, or the decrease of the target dosage as determined at 758, may be used to determine the amount of therapy dosage up-titration at 741 and the therapy dosage down-titration at 742. The up- or down-titration of therapy dosage may follow a specified titration mode that indicates a rate of change of therapy dosage, or a temporal profile of the change of therapy dosage. By way of example and not limitation, FIGS. 4A-B illustrated step-wise up-titration and step-wise down-titration modes. Other examples of the titration mode may include linear, piecewise linear, exponential, parabolic, or other non-linear functions.

At 760, a therapy dosage profile may be generated using the therapy titrations at 741 and 742 or the maintained therapy dosage at 743 at different time. The therapy dosage profile, which is a part of the therapy titration protocol, may be presented to a user such as a clinician at 652, or to be used to guide therapy delivery at 654.

Figure 8:
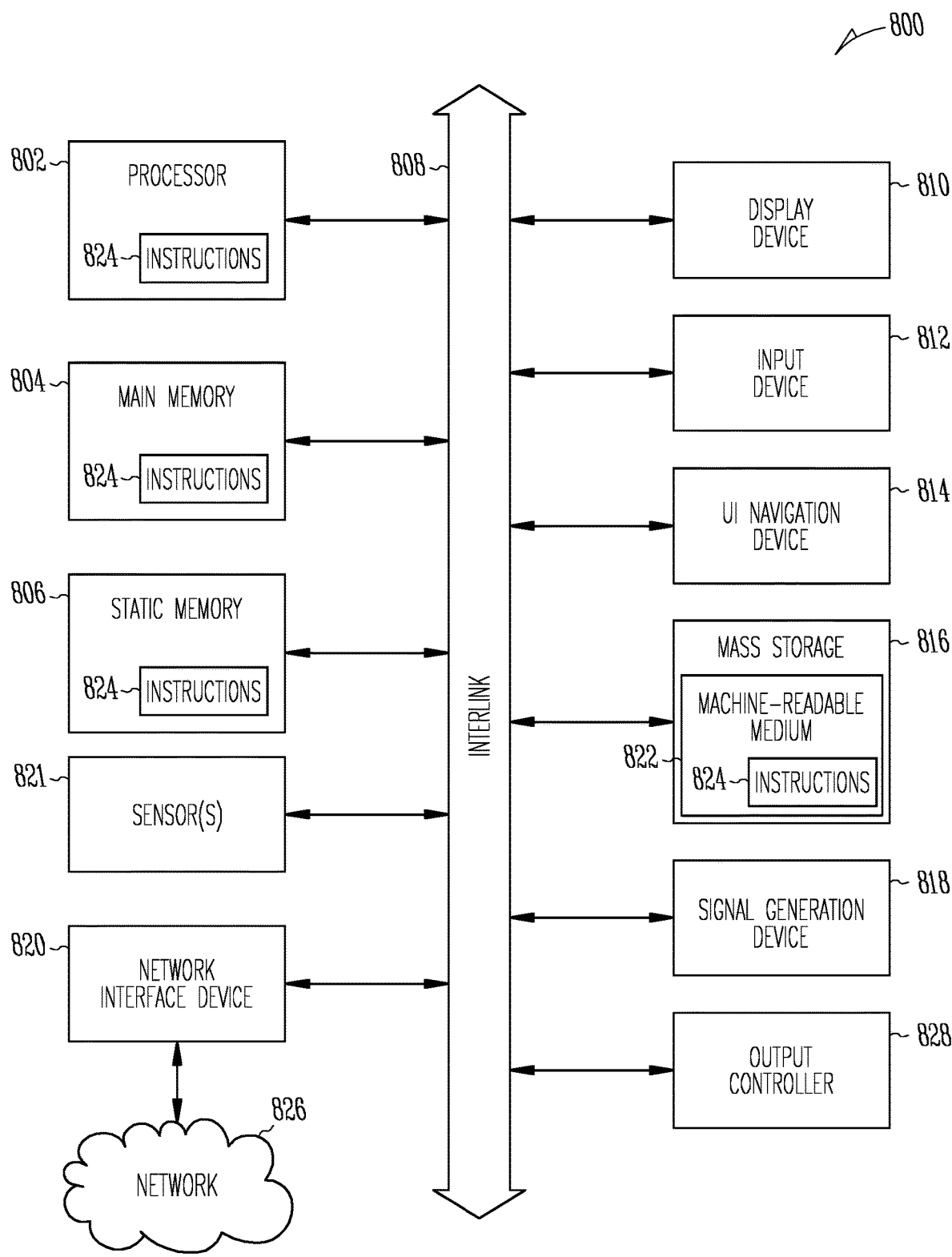
FIG. 8 illustrates generally a block diagram of an example machine upon which any one or more of the techniques (e.g., methodologies) discussed herein may perform.

FIG. 8 illustrates generally a block diagram of an example machine 800 upon which any one or more of the techniques (e.g., methodologies) discussed herein may perform. Portions of this description may apply to the computing framework of various portions of the LCP device, the IMD, or the external programmer.

In alternative embodiments, the machine 800 may operate as a standalone device or may be connected (e.g., networked) to other machines. In a networked deployment, the machine 800 may operate in the capacity of a server machine, a client machine, or both in server-client network environments. In an example, the machine 800 may act as a peer machine in peer-to-peer (P2P) (or other distributed) network environment. The machine 800 may be a personal computer (PC), a tablet PC, a set-top box (STB), a personal digital assistant (PDA), a mobile telephone, a web appliance, a network router, switch or bridge, or any machine capable of executing instnictions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 800 may include a hardware processor 802 (e.g., a central processing unit (CPU), a graphics processing unit (GPU), a hardware processor core, or any combination thereof), a main memory 804 and a static memory 806, some or all of which may communicate with each other via an interlink (e.g., bus) 808. The machine 800 may further include a display unit 810 (e.g., a raster display, vector display, holographic display, etc.), an alphanumeric input device 812 (e.g., a keyboard), and a user interface (UI) navigation device 814 (e.g., a mouse). In an example, the display unit 810, input device 812 and UI navigation device 814 may be a touch screen display. The machine 800 may additionally include a storage device (e.g., drive unit) 816, a signal generation device 818 (e.g., a speaker), a network interface device 820, and one or more sensors 821, such as a global positioning system (GPS) sensor, compass, accelerometer, or other sensor. The machine 800 may include an output controller 828, such as a serial (e.g., universal serial bus (USB), parallel, or other wired or wireless (e.g., infrared (IR), near field communication (NFC), etc. connection to communicate or control one or more peripheral devices (e.g., a printer, card reader, etc.).

The storage device 816 may include a machine readable medium 822 on which is stored one or more sets of data structures or instructions 824 (e.g., software) embodying or utilized by any one or more of the techniques or functions described herein. The instructions 824 may also reside, completely or at least partially, within the main memory 804, within static memory 806, or within the hardware processor 802 during execution thereof by the machine 800. In an example, one or any combination of the hardware processor 802, the main memory 804, the static memory 806, or the storage device 816 may constitute machine readable media.

While the machine-readable medium 822 is illustrated as a single medium, the term "machine readable medium" may include a single medium or multiple media (e.g., a centralized or distributed database, and/or associated caches and servers) configured to store the one or more instructions 824.

The term "machine readable medium" may include any medium that is capable of storing, encoding, or carrying instructions for execution by the machine 800 and that cause the machine 800 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine readable medium with a plurality of particles having invariant (e.g., rest) mass. Accordingly, massed machine-readable media are not transitory propagating signals. Specific examples of massed machine-readable media may include: non-volatile memory, such as semiconductor memory devices (e.g., Electrically Programmable Read-Only Memory (EPROM), Electrically Erasable Programmable Read-Only Memory (EPSOM)) and flash memory devices; magnetic disks, such as internal hard disks and removable disks; magneto-optical disks; and CD-ROM and DVD-ROM disks.

The instructions 824 may further be transmitted or received over a communication network 826 using a transmission medium via the network interface device 820 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 820 may include one or more physical jacks (e.g., Ethernet, coaxial, or phone jacks) or one or more antennas to connect to the communication network 826. In an example, the network interface device 820 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 800, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should therefore be determined with references to the appended claims, along with the full scope of equivalents to which such claims are entitled.

What is claimed is:

1. A system for adjusting a therapy dosage in a patient, comprising:

a receiver circuit configured to receive physiological signals, and to receive a target dosage representing a baseline dosage of a therapy;

a physiological event detector circuit configured to: generate a composite signal metric from at least two of the received physiological signals; generate a composite signal metric trend by trending the composite signal metric over time during a progression of a physiological condition; and detect a physiological event using the generated composite signal metric trend; and a therapy control circuit coupled to the physiological event detector circuit, the therapy control circuit configured to generate a therapy titration protocol including generating a temporal profile of therapy dosage by varying the therapy dosage relative to the target dosage in accordance with the generated composite signal metric trend, wherein the therapy control circuit is configured to down-titrate the therapy dosage in response to the generated composite signal metric trend falling below a specific threshold and indicating a decreased trend.

2. The system of claim 1, comprising a therapy delivery unit configured to initiate or adjust a therapy according to the therapy titration protocol in response to the detection of the physiological event.

3. The system of claim 1, wherein the physiological event detector circuit is configured to detect a worsening heart failure (WHF) event, and the therapy control circuit is configured to generate a heart failure therapy titration protocol using the generated composite signal metric trend.

4. The system of claim 3, wherein the heart failure therapy titration protocol includes a temporal profile of drug dosage relative to a target drug dosage for treating the detected WHF event.

5. The system of claim 1, wherein the therapy control circuit is configured to up-titrate the therapy dosage in response to the generated composite signal metric trend exceeding a physiological event onset threshold and indicating an increase trend.

6. The system of claim 1, wherein the therapy control circuit is configured to adjust the target dosage using a comparison of the temporal profile of therapy dosage and the target dosage.

7. The system of claim 6, wherein the therapy control circuit is configured to, when the temporal profile of therapy dosage is above the target dosage for a first time period, increase the target dosage to a level corresponding to a lowest therapy dosage achieved during the first time period.

8. The system of claim 6, wherein the therapy control circuit is configured to:

down-titrate the therapy dosage to a level lower than the target dosage;

evaluate patient response to the down-titrated therapy dosage over a second time period; and decrease the target dosage to a level corresponding to the down-titrated therapy dosage if the evaluated patient response indicates no worsening of the physiological condition during the second time period.

9. The system of claim 8, wherein the patient response includes a composite signal metric trend corresponding to the down-titrated therapy dosage, and the therapy control circuit is configured to decrease the target dosage if the composite signal metric trend is within a specific range indicating no worsening of the physiological condition during the second time period.

10. The system of claim 1, wherein the physiological event detector circuit is configured to generate the composite signal metric using a heart sound signal and a respiration signal.

11. The system of claim 10, wherein the composite signal metric is a combination of an S3 heart sound metric generated from the heart sound signal and a respiration rate metric generated from the respiration signal.

12. The system of claim 11, wherein the respiration rate metric includes a ratio of a respiration rate to a tidal volume, the respiration rate and the tidal volume generated from the respiration signal.

* * * * *